United States Statutory Invention Registration [19]

[11] Reg. Number: H234

Gilbert [43] Published: Mar. 3, 1987

[54] ENERGETIC DERIVATIVES OF A NOVEL DIOL AND METHODS FOR THEIR SYNTHESES

[75] Inventor: Everett E. Gilbert, Morristown, N.J.

[73] Assignee: The United States of America as represented by the Secretary of the Army, Washington, D.C.

[21] Appl. No.: 767,921

[22] Filed: Aug. 21, 1985

[51] Int. Cl.[4] ..... C07C 117/00; C07C 77/02; C06B 25/04

[52] U.S. Cl. ..... 260/349; 149/105; 149/19.4; 558/482

[58] Field of Search ..... 260/466, 349

[56] References Cited

U.S. PATENT DOCUMENTS

| | | | |
|---|---|---|---|
| 1,620,714 | 3/1927 | Bergeim | 260/349 |
| 1,824,848 | 9/1931 | Turek | 260/349 X |
| 2,912,456 | 11/1959 | Fookes | 260/466 |
| 3,770,779 | 11/1973 | Kiehs et al. | 260/349 |
| 3,948,957 | 4/1976 | Beck | 260/349 |

OTHER PUBLICATIONS

Gilbert; J. Energ. Mater., 2(3), pp. 215–228.

Boschan, et al.; Chem. Reviews, 55, (1955), pp. 485 and 488.

Boyer, et al.; Chem. Reviews, 54, (1954), pp. 1, 2 and 9.

*Primary Examiner*—John F. Terapane
*Assistant Examiner*—J. E. Thomas
*Attorney, Agent, or Firm*—Anthony Lane; Robert Gibson; Edward F. Costigan

[57] ABSTRACT

A novel diol, 1,3-Bis-2(2-hydroxyethyl)-2,4,6-trinitrobenzene has been synthesized by the reaction of 1,3-dimethyl-2,4,6-trinitrobenzene with formaldehyde. The novel diol can be converted to a dinitrate and to a diazide which are both useful as explosives or as propellants.

4 Claims, No Drawings

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

ENERGETIC DERIVATIVES OF A NOVEL DIOL AND METHODS FOR THEIR SYNTHESES

The invention described herein may be manufactured, used and licensed by or for the Government for Governmental purposes without the payment to me of any royalties thereon.

This invention relates to a novel diol and in particular to the dinitrate and diazide derivatives of such diol. Also included within the scope of the invention is a polymeric product derived from the reaction of such diol with hexamethylene diisocyanate.

By way of general background it should be noted that the reaction of trinitrotoluene (TNT) with formaldehyde to form the alkanol 1-(2-hydroxyethyl)-2,4,6-trinitrobenzene is known. See Chem. Abstracts 10, 1513 (1916). However, the extension of this reaction to homologues of TNT is not known. Although the trimethyl homologue of TNT only leads to a monohydroxy product it has now been surprisingly discovered that the dimethyl homologue of TNT reacts with formaldehyde to form a diol. See the commonly assigned patent application (attorney Docket No. DAR 30-84) filed on even date herewith under Ser. No. 767,994 and Journal of Energetic Materials vol. 2, 215–228 (September 1984), published by Dowden, Brodman & Devine, Inc. The disclosures contained in the aforesaid patent document and in the aforesaid publication are hereby incorporated in their entireties by this reference thereto.

According to the present invention, it has now been discovered that the novel diol referred to above can be converted to a dinitrate and to a diazide. Moreover, a polyester derivative of the diol is also obtained by reacting the diol with hexamethylene diisocyanate. Since the alkanols derived from TNT and from its trimethyl homologue are both monohydroxy, only mononitro and monoazide derivatives thereof are obtainable. However, the novel unexpectedly synthesized diol underlying the present invention permits the synthesis of dinitro and diazide derivatives. Both of the nitro and azide groups are well known for their energetic (explosive) power. Thus, the surprising discovery that two rather than one of the nitro and/or azide groups can be attached to a methyl homolog of the well-known explosive TNT has resulted in the synthesis of such dinitro and such diazide derivatives of correspondingly (and therefore unexpectedly) superior energetic output.

According to the present invention there is therefore provided a novel 2,4,6-trinitrobenzene derivative containing $R_1$, $R_2$ and $R_3$ attachments in the 1,3 and 5-positions respectively wherein (a) $R_1$ is a substituent selected from the group consisting of $CH_2CH_2ONO_2$ and $—CH_2CH_2N_3$;

(b) $R_2$ is a substituent selected from the group consisting of $—CH_2CH_2ONO_2$ and $—CH_2CH_2N_3$; and (c) $R_3$ is hydrogen In another aspect of the present invention, a method is provided for the synthesis of the dinitro derivative of the novel diol underlying the present invention, i.e., 1,3-Bis(2-nitroxethyl)-2,4,6-trinitro-benzene which comprises the step of reacting together in a mixture 1,3-Bis(2-hydroxyethyl)-2,4,6-trinitrobenzene with nitric acid to yield said compound as a reaction product.

In still another aspect of the present invention, a method is provided for the synthesis of the diazide derivative of the novel diol underlying the present invention, i.e., 1,3-Bis(2-azidoethyl)-2,4,6-trinitrobenzene which comprises the step of reacting together in a mixture 1,3-Bis(2-nitroxyethyl)-2,4,6-trinitrobenzene with sodium azide to yield said compound as a reaction product.

In yet another aspect of the present invention, a polymeric product is provided which is obtained by the reaction of 1,3-Bis(2-hydroxyethyl)-2,4,6-trinitrobenzene with hexamethylene diisocyanate by a process which comprises the steps of (a) reacting the 1,3-Bis(2-hydroxyethyl)-2,4,6-trinitrobenzene with hexamethylene diisocyanate in a dimethylformamide solvent with stirring for about 6 hours at a temperature of about 100 degrees Celcius to form a reaction mixture with a solid precipitate;

(b) cooling the reaction mixture;

(c) thereafter filtering the reaction mixture to recover the solid precipitate; and (d) washing the solid precipitate with acetone.

The following illustrative, but non-limiting examples will aid in a fuller understanding of the present invention.

Example 1

For the purposes of this, and all the succeeding examples the ready availability of the novel diol underlying the present invention, i.e., 1,3-Bis(2-hydroxyethyl)-2,4,6-trinitrobenzene (hereinafater referred to as "the diol") is assumed. A method for the synthesis of the diol is included in Journal of Energetic Materials vol 2, 215–228 (September 1984) published by Dowden, Brodman & Devine, Inc.

4.0 g of the diol, 12 ml of 90% w/w aqueous nitric acid and 35 ml methylene chloride are stirred in a test tube for 1 hour in the temperature range of 5 to 10 degrees Celcius. The resulting solution is washed with ice water, dried, and the solvent is removed giving a viscous oil which soon solidifies. The solid dinitro product, namely, 1,3-Bis(2-nitroxyethyl)-2,4,6-trinitrobenzene is recrystallized from a butanol solution.

The dinitro product has a melting point of 87 degrees Celcius. The infrared spectrum of the dinitro product shows absorption bands in the characteristic frequencies (in reciprocal centimeters) for a nitro group at 1340 and 1550 and for a nitroxyl group at 1340, 1280 and 860. Elemental analysis of the dinitro product for C and H agrees with the predicted theoretical proportions.

Upon heating the dinitro product upon a spatula over a low Bunsen flame the said dinitro product is seen to flash brightly in a positive match test. This test establishes the utility of the dinitro compound as an explosive or as a propellant.

Example 2

0.4 g of 1,3-Bis(2-nitroxyethyl)-2,4,6-trinitrobenzene prepared as described in Example 1 above is mixed with 2.4 g sodium azide and 15 ml acetic acid. The mixture is stirred for 41 hours in the 70 to 75 degrees Celcius temperature range. The reaction mixture is thereafter poured into water and the diazide reaction product, namely, 1,3-Bis(2-azidoethyl)-2,4,6-trinitrobenzene is thereafter extracted from the resulting aqueous phase with the use of methylene chloride. The methylene chloride solution is dried and the methylene chloride solvent removed by distillation to yield a viscous oil product which does not crystallize.

The infrared spectrum of the product indicates that it is free from the nitrate groups contained in one of the precursor reactants but that it does contain azide and nitro groups.

The product residue gives a positive match test (see Example 1 above) thereby establishing the utility of the diazide compound as an explosive or as a propellant.

Example 3

1.5 g of the diol is mixed with an equimolar quantity (0.85 g) of hexamethylene diisocyanate and 25 ml of dimethylformamide. The resulting mixture is heated with stirring for 6 hours at 100 degrees Celcius. A solid product separates out during the latter portion of the heating period. The reaction mixture is thereafter cooled and filtered. The filtered solid product is washed with acetone to furnish a 0.5 g yield of a polymeric product. The polymeric product darkens, but does not melt, upon heating to 300 degrees Celcius.

The scope of the present invention is further defined by and should be read in conjunction with the appended claims.

What is claimed is:

1. 1,3-Bis-(2-nitroxyethyl)-2,4,6-trinitrobenzene.

2. 1,3-Bis-(2-azidoethyl)-2,4,6-trinitrobenzene.

3. The process of making 1,3-Bis-(2-nitroxyethyl)-2,4,6-trinitrobenzene by reacting in ratio of about 4.0 g of 1,3-Bis-(2-hydroxyethyl)-2,4,6-trinitrobenzene with about 12 ml of 90% aqueous nitric acid and about 35 ml. methylene chloride for about 1 hour at a temperature between about 5° C. and 10° C.

4. The process of making 1,3-Bis-(2-azidoethyl)-2,4,6-trinitrobenzene by reacting in ratio about 0.4 g of 1,3-Bis-(2-nitroxyethyl)-2,4,6-trinitrobenzene with about 2.4 g sodium azide and about 15 ml. acetic acid, with stirring, for about 41 hours at a temperature between about 70° C. and 75° C., pouring into water, and extracting with methylene chloride.

* * * * *